US009364261B2

(12) United States Patent  
Hector, Jr.

(10) Patent No.: US 9,364,261 B2
(45) Date of Patent: Jun. 14, 2016

(54) APPARATUS AND METHOD FOR REMOVING A FOREIGN OBJECT FROM A RECTAL CAVITY

(71) Applicant: Melvin G Hector, Jr., Tucson, AZ (US)

(72) Inventor: Melvin G Hector, Jr., Tucson, AZ (US)

(73) Assignee: Melvin G. Hector, Jr., Tucson, AZ (US)

( * ) Notice: Subject to any disclaimer, the term of this patent is extended or adjusted under 35 U.S.C. 154(b) by 0 days.

(21) Appl. No.: 14/269,005

(22) Filed: May 2, 2014

(65) Prior Publication Data

US 2014/0343368 A1    Nov. 20, 2014

Related U.S. Application Data

(60) Provisional application No. 61/823,149, filed on May 14, 2013.

(51) Int. Cl.
| | | |
|---|---|---|
| *A61B 1/32* | (2006.01) |
| *A61B 17/50* | (2006.01) |
| *A61B 1/31* | (2006.01) |
| *A61B 17/221* | (2006.01) |
| *A61B 17/00* | (2006.01) |
| *A61B 17/34* | (2006.01) |

(52) U.S. Cl.
CPC . *A61B 17/50* (2013.01); *A61B 1/31* (2013.01); *A61B 17/221* (2013.01); *A61B 2017/00358* (2013.01); *A61B 2017/2215* (2013.01); *A61B 2017/3452* (2013.01)

(58) Field of Classification Search
CPC ......... A61B 17/50; A61B 1/31; A61B 17/221
See application file for complete search history.

(56) References Cited

U.S. PATENT DOCUMENTS

| | | | | |
|---|---|---|---|---|
| 5,749,879 | A | * | 5/1998 | Middleman et al. .......... 606/139 |
| 5,759,187 | A | * | 6/1998 | Nakao et al. .................. 606/114 |
| 2006/0058776 | A1 | * | 3/2006 | Bilsbury ....................... 604/540 |
| 2008/0306336 | A1 | * | 12/2008 | Kaye et al. .................... 600/106 |
| 2009/0192510 | A1 | * | 7/2009 | Bahney ............................ 606/45 |
| 2010/0042107 | A1 | * | 2/2010 | Merrifield ..................... 606/106 |
| 2010/0241134 | A1 | * | 9/2010 | Odon et al. .................... 606/123 |
| 2012/0116336 | A1 | * | 5/2012 | Sharma ................... A61F 5/451 604/328 |
| 2014/0121672 | A1 | * | 5/2014 | Folk ............................... 606/127 |
| 2014/0213847 | A1 | * | 7/2014 | Green et al. ................... 600/104 |
| 2014/0276910 | A1 | * | 9/2014 | Smith et al. ................... 606/113 |
| 2015/0025555 | A1 | * | 1/2015 | Sos ............................... 606/159 |

OTHER PUBLICATIONS

Kasotakis et al., Rectal foreign bodies: A case report and review of the literature, 2012, Int J Surg Case Rep., 3(3), 111-115.*

* cited by examiner

*Primary Examiner* — Ellen C Hammond

(57) ABSTRACT

A new and useful apparatus and method are provided for removing a foreign object from a rectal cavity. An anoscope is configured for insertion through the anus into a rectal cavity. The anoscope has a base and introducer with guides that route flexible members and a flexible sheath that are carried by actions of the operator through the anoscope beyond the guide and further into a rectal cavity and to expand about a foreign object in the rectal cavity. The anoscope also carries a noose that is manipulatable from outside the patient's rectal cavity to tighten and stricture the flexible sheath above the foreign object and capture the foreign object within the flexible sheath, so that the foreign object can be manipulated by the noose and the flexible sheath to remove the foreign object from the rectal cavity once the anoscope and flexible ribs are removed from the anus.

3 Claims, 12 Drawing Sheets

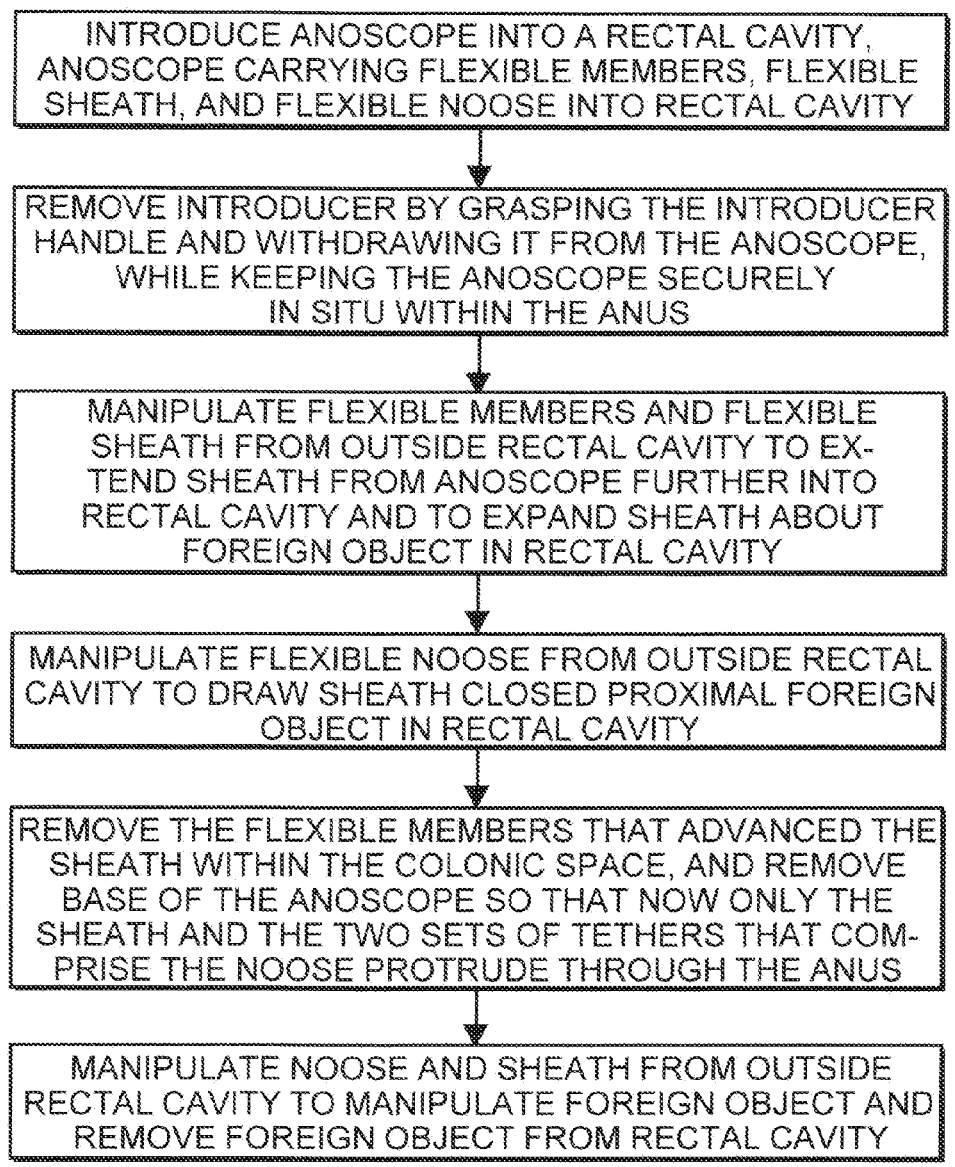

APPARATUS AND METHOD FOR REMOVING A FOREIGN OBJECT FROM A RECTAL CAVITY

RELATED APPLICATION/CLAIM OF PRIORITY

This application is related to and claims priority from U.S. provisional application Ser. No. 61/823,149, filed May 14, 2013, which provisional application is incorporated by reference herein.

BACKGROUND AND SUMMARY OF THE INVENTION

The present invention relates to a new and useful apparatus and method for removing a foreign object from a rectal cavity. In the experience of medical practitioners, when a foreign object becomes lodged in a rectal cavity, removing the foreign object often requires surgery that can expose the patient to conditions that would be desirable to avoid, if possible. An Article Entitled "Foreign Objects In The Rectum" dated July '08 and published by the Arizona Department of Corrections, Heath Services Bureau, Inmate Wellness Program HEP 1042, and an article entitled "Rectal foreign bodies; A case report and review of the literature", by G. Kasotakis, L. Roediger and S. Mittal, Int J Surg Case Rep, 2012, 3(3): 111-115, Published online Dec. 8, 2011, both of which are incorporated by reference herein, further explain the potential issues attendant with removal of a foreign object from a rectal cavity.

The present invention seeks to address these issues, by providing an apparatus and a method by which a foreign object can often be removed from a rectal cavity without the need for a surgical procedure and its inherent risks. In this application, the term "rectal cavity" means the distal colon proximal to the anus, any or all parts of a colon and any human cavity portions that extend proximal to the anus. A "foreign object" means an object that has been inserted into the rectal cavity through the anus and would not normally be found in the rectal cavity of a human body.

According to the invention, the apparatus for removing a foreign object from a rectal cavity, comprises an anoscope configured for insertion through the anus into a rectal cavity. The anoscope has a base with guides that route flexible members within a flexible sheath that are in action carried through the anoscope beyond the guide and further into a rectal cavity and expand about a foreign object in the rectal cavity. The anoscope also carries a noose that is held by the flexible members and is manipulatable from outside the patient's rectal cavity to tighten and stricture the flexible sheath above the foreign object and capture the foreign object within the flexible sheath, so that the foreign object can be manipulated by the noose and the flexible sheath to remove the foreign object from the rectal cavity.

In a preferred apparatus, the anoscope base has guides for a plurality of flexible ribs that are guided by the anoscope into the rectal cavity. The flexible ribs are disposed inside the flexible sheath, and are connected with the flexible sheath in a manner such that the flexible ribs can be extended from the anoscope base further into a rectal cavity, and expand as they extend beyond the anoscope base to expand the flexible sheath about a foreign object in the rectal cavity. The noose comprises a radiopaque strand (and preferably a pair of such strands) that is (are) guided by the anoscope base and connected with the flexible sheath in a manner such that the noose can be manipulated to draw the flexible sheath closed above the foreign object and proximal to the foreign object within the rectal cavity, allowing the sheath to then form an enclosure within which the foreign object may be safely retracted distally and removed from the rectal cavity.

According to the method of the invention for removing a foreign object from a rectal cavity,
a. an anoscope base (that includes a base member and introducer) is lubricated and then inserted into a rectal cavity, and carries flexible members and a flexible sheath that are configured to extend from the anoscope base further into a rectal cavity and to expand about a foreign object in the rectal cavity;
b. the anoscope base carries a flexible noose that is manipulated from outside the rectal cavity to draw the flexible sheath closed above the foreign object and proximal to the foreign object within the rectal cavity and capture the foreign object within the flexible sheath, which is then manipulated in a manner that tracts the foreign object distally to remove the foreign object from the rectal cavity through the anus.

In the preferred way of practicing the applicant's method, the anoscope base and flexible members are withdrawn from the rectal cavity before the noose and flexible sheath are manipulated to tract the foreign object distally and remove it from the rectal cavity.

Further features of the present invention will become apparent from the following detailed description and the accompanying drawings.

BRIEF DESCRIPTION OF THE DRAWINGS

FIGS. 1(*a-d*), 2(*a-c*) and 3(*a-c*) are schematic illustrations of parts of an apparatus for removing a foreign object from a rectal cavity, according to the invention;

FIG. 6 is a schematic illustration of the method for removing a foreign object from a rectal cavity, according to the method of the invention.

DETAILED DESCRIPTION

As discussed above, the present invention relates to a new and useful apparatus and a method by which a foreign object can often be removed from a rectal cavity without the need for a surgical procedure and its inherent risks. The invention is described herein in connection with one example of the apparatus, and from that description the manner in which the invention can be practiced with apparatus and methods that exemplify the principles of the present invention will be apparent to those skilled in the art.

Figure 1:
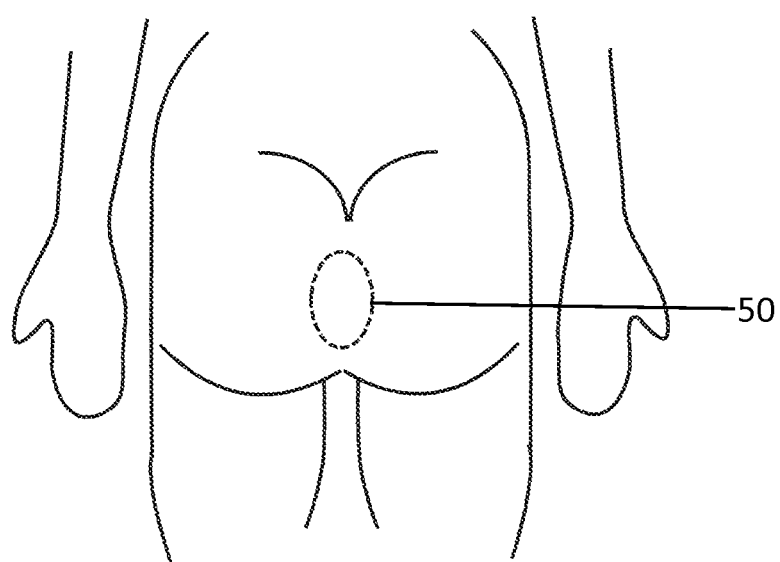
FIG. 1 schematically illustrates one type of foreign object that can become lodged in a rectal cavity.
Figure 1A:
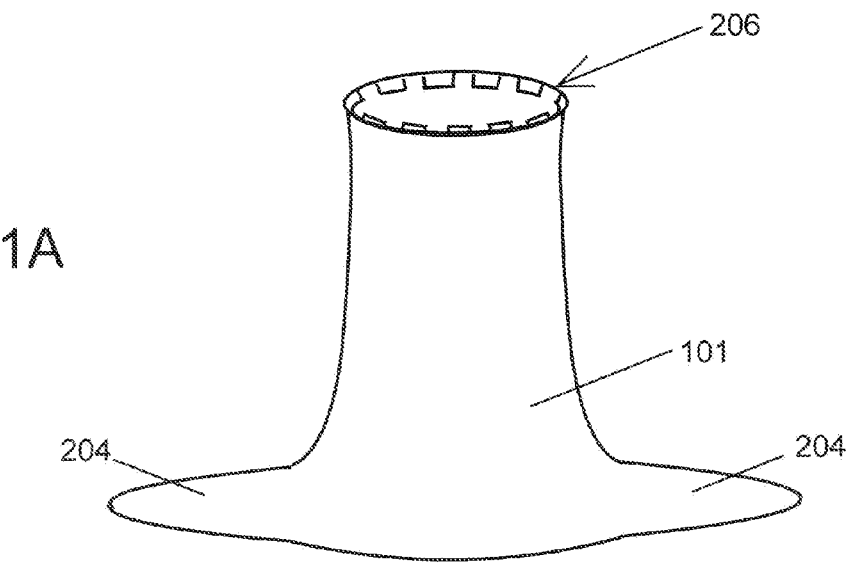
Figure 1B:
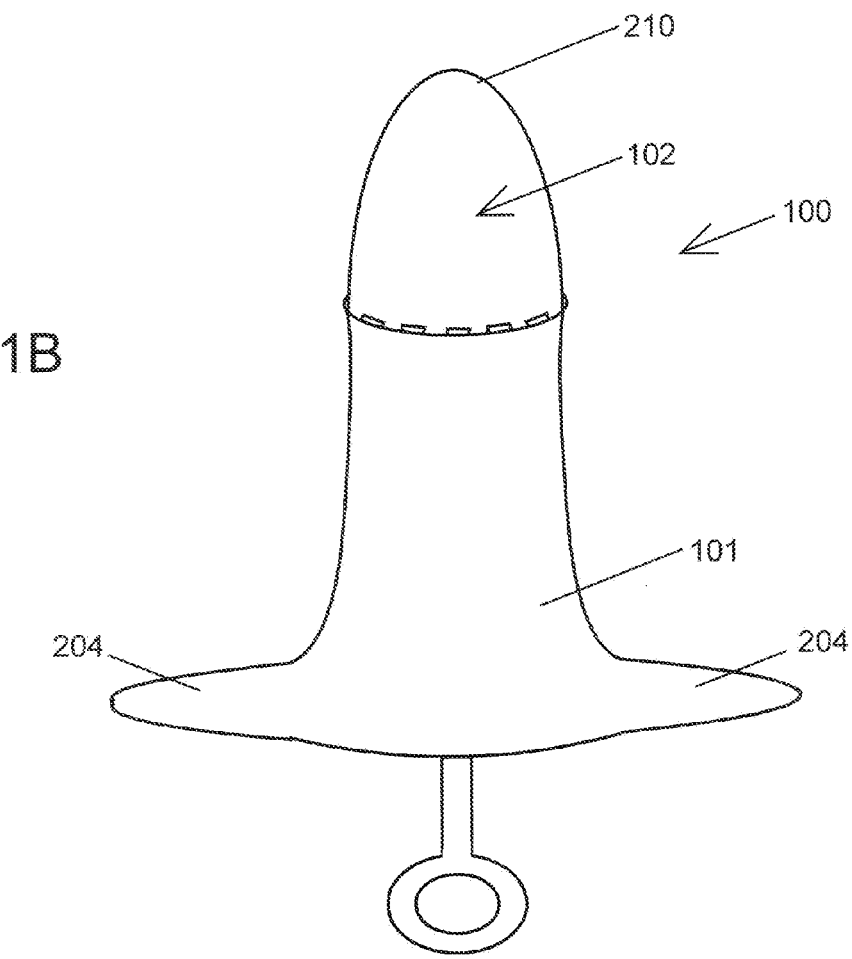
Figure 1C:
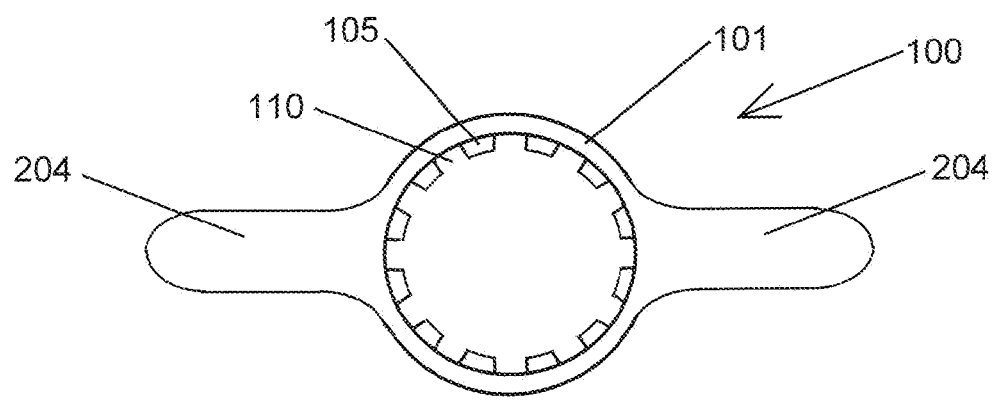
Figure 1D:
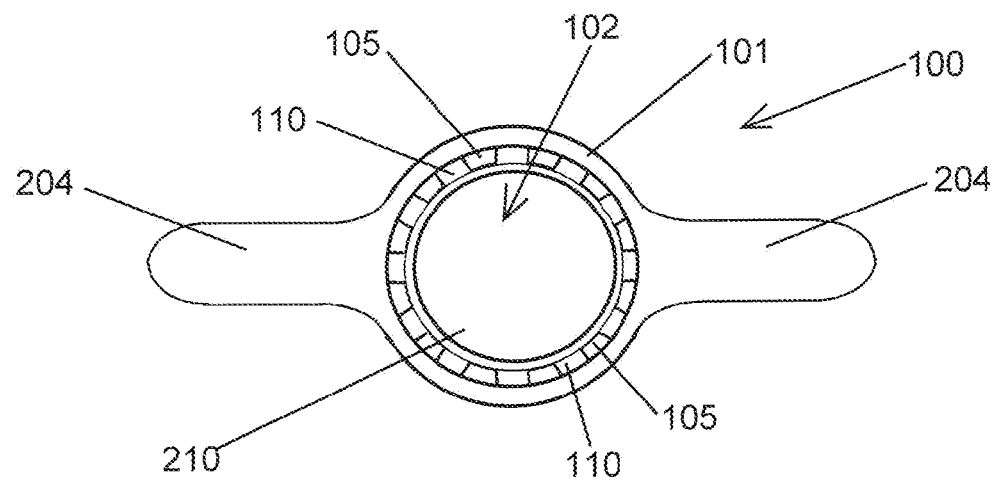

FIG. 1 shows an example of a type of foreign object (e.g. an egg 50) that can become lodged in a rectal cavity, and which the apparatus and method of the invention is designed to remove.

The apparatus, which is described in more detail below, is shown in FIGS. 1-5. A two piece anoscope 100 is configured for insertion through the patient's anus and into the patient's rectal cavity. The anoscope 100 includes a base (which is preferably a base member 101 that is connected with an introducer 102), and is configured for insertion into a rectal cavity. The anoscope base 101 has guide slots 110 for flexible rib members 112 that carry the flexible sheath beyond the anoscope base and expand the flexible sheath about a foreign object in the rectal cavity. The tips 301 of the flexible ribs 112 also act on a looped portion 300 of the sheath in which the flexible noose 108 is carried, so that the flexible radiopaque noose 108 (that preferably comprises a pair of noose strands 108A, 108B that extend out of the looped portion 300 at diametrically opposed locations on the sheath 106) can also be extended with the sheath beyond the guides and further into a rectal cavity and expand with the flexible sheath 106 about a foreign object in the rectal cavity. The flexible noose strands 108A, 108B are then manipulatable from outside the patient's rectal cavity in a drawstring type closure to tighten and stricture the flexible sheath 106 "above" the foreign object and capture the foreign object within the flexible sheath, so that the foreign object can eventually be manipulated by the noose and the flexible sheath to deliver the foreign object from the rectal cavity.

Figure 5A:
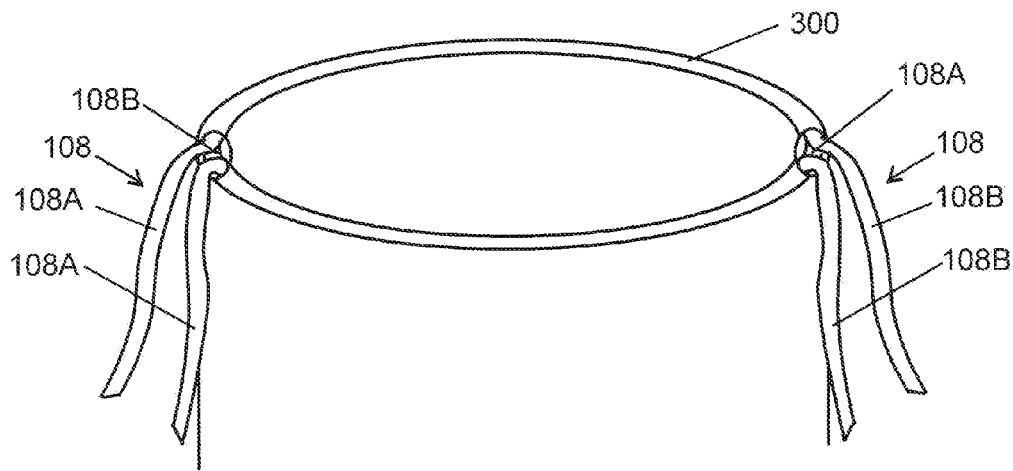
FIG. 5 (*a-g*) schematically illustrate additional parts and some additional steps of an apparatus and method for removing a foreign object from a rectal cavity, according to the invention.
Figure 5B:
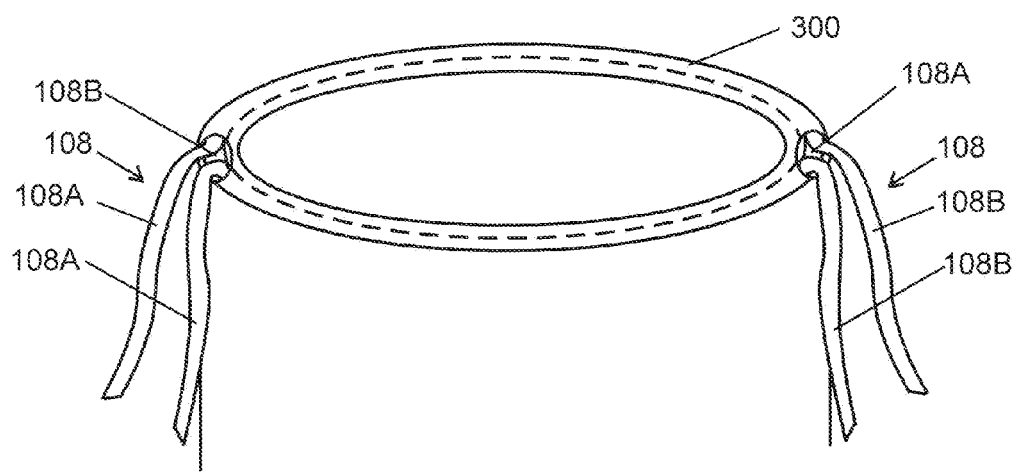
Figure 5C:
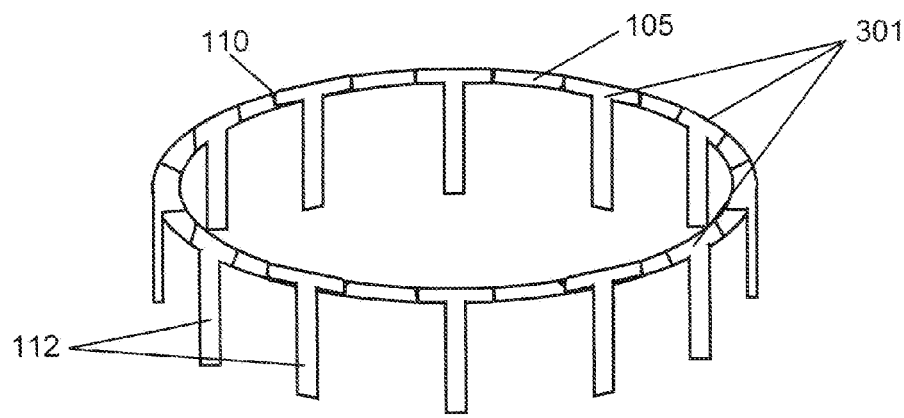
Figure 5D:
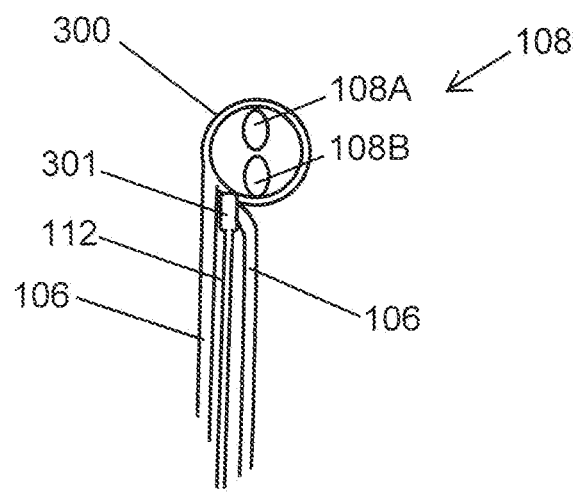
Figure 5E:
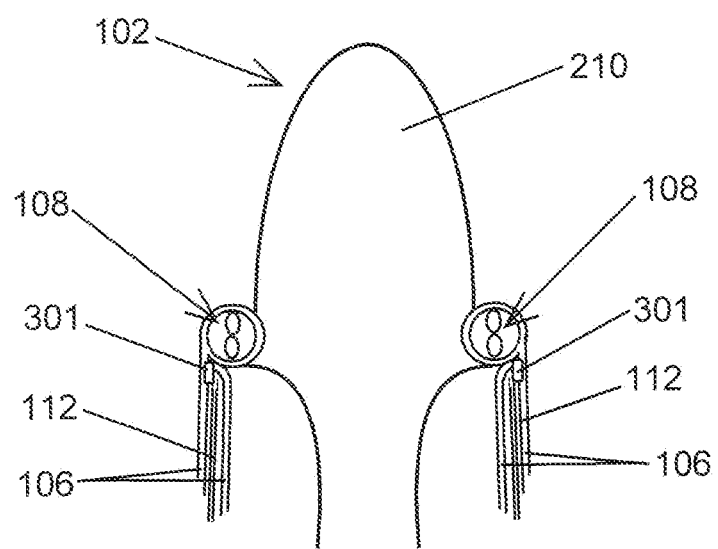
Figure 5F:
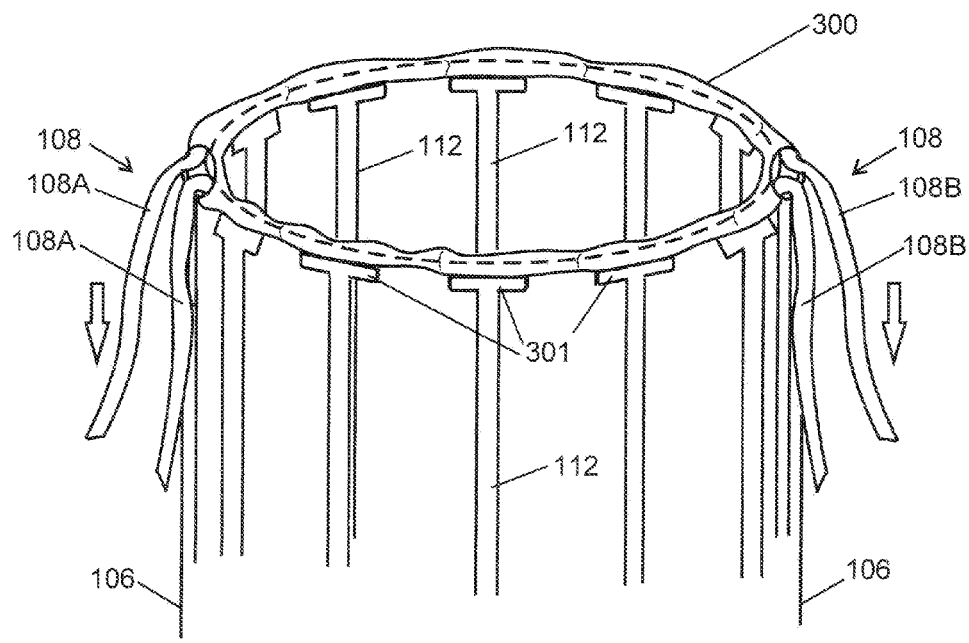
Figure 5G:
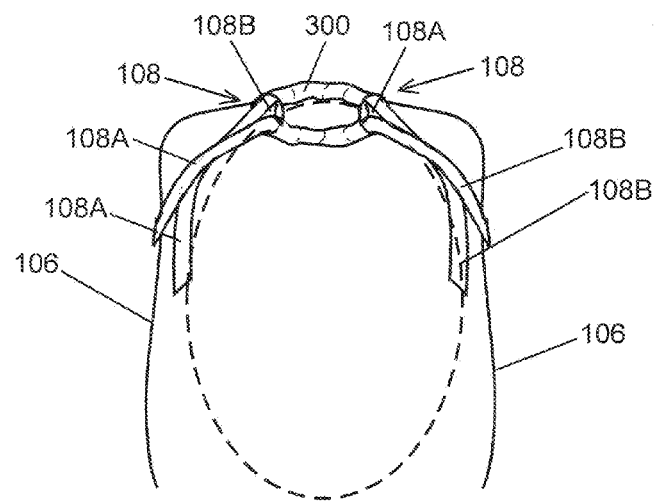

In a preferred apparatus, the anoscope base member 101 has guide slots 110 for a plurality of flexible ribs 112 that are guided by the anoscope into the rectal cavity. The flexible sheath 106 comprises a doubled-over sheath member that is heat sealed on itself at its leading edge to create the looped portion 300 as a guide for the flexible noose 108 and a closed inside border within the anoscope base, and the flexible ribs 112 are disposed inside the flexible sheath, with their tips 301 located against the inside border of the guide 300 (and initially supported by the shelves 105 of the base member that are located between the guide slots 110) such that, once the introducer 102 is removed from the anoscope base 101, the flexible ribs can be extended from the anoscope base further into a rectal cavity, and expand as they extend beyond the anoscope base to expand the flexible sheath including the looped portion 300 about a foreign object in the rectal cavity (see e.g. FIG. 5g). As schematically illustrated in FIGS. 5g and 5h, the noose 108 (which preferably comprises the pair of flexible radiopaque strands 108A, 108B that are carried by the looped portion 300 of the flexible sheath), so that the noose is carried by the flexible sheath as it is expanded by the flexible ribs, and once the flexible sheath has been expanded to extend about a foreign object in a rectal cavity, the noose strand(s) 108A, 108B can be manipulated to draw the flexible sheath closed above the foreign object (see e.g. FIG. 5h) and manipulate the noose, closing the flexible sheath proximal to and about the foreign object within the rectal cavity, allowing the sheath to then form an enclosure within which the foreign object may be safely retracted distally and removed from the rectal cavity.

Figure 2A:
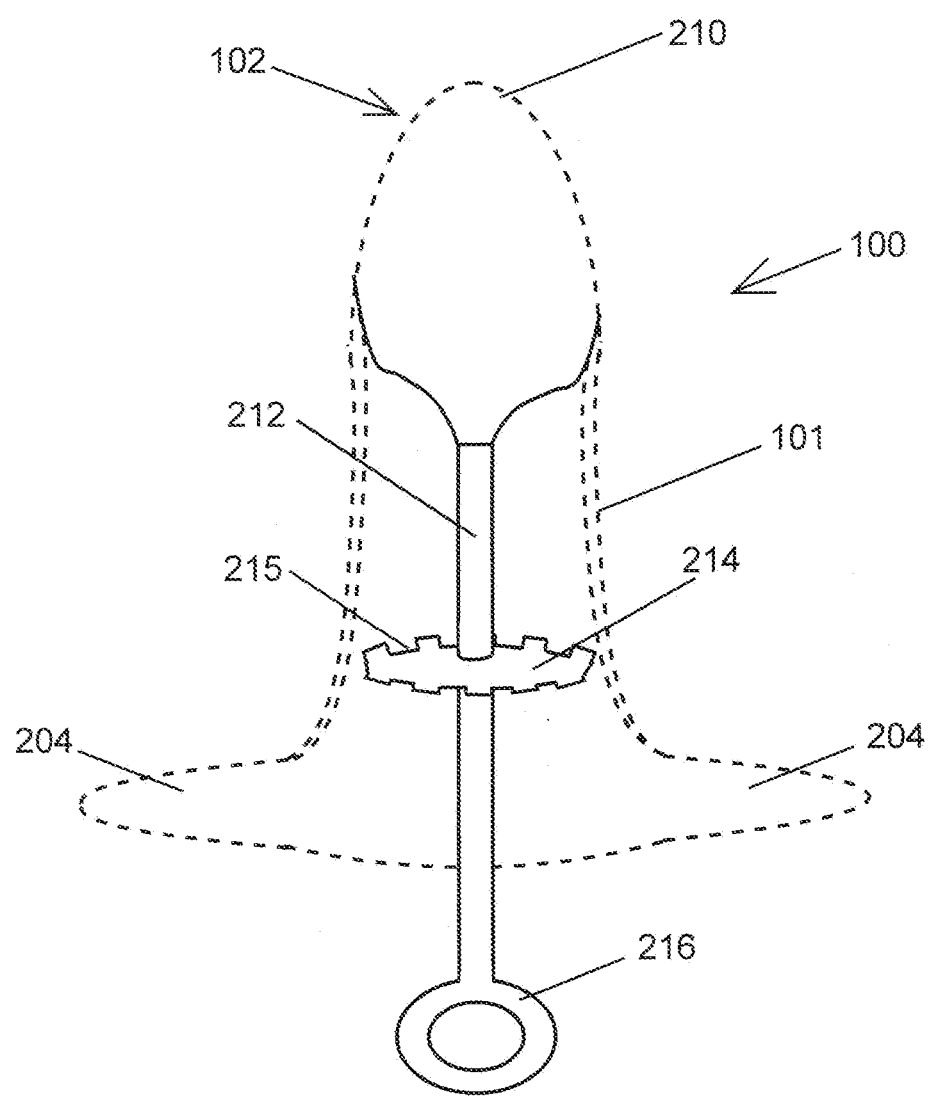
Figure 2B:
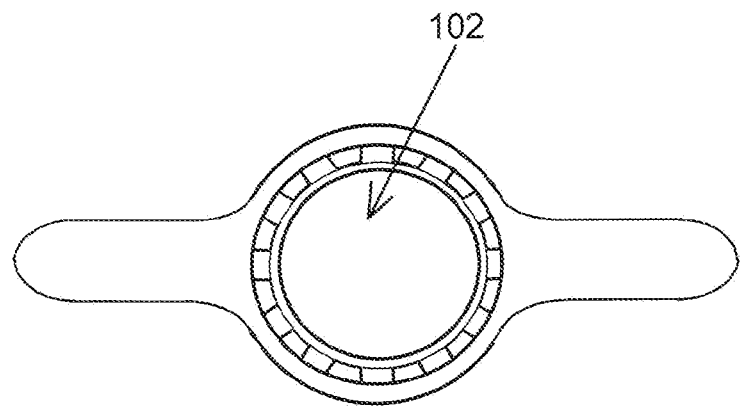
Figure 2C:
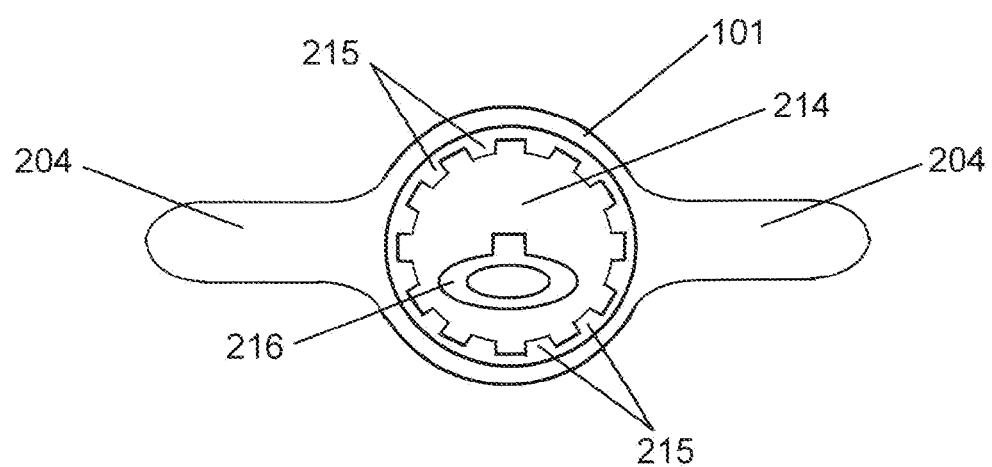
Figure 3A:
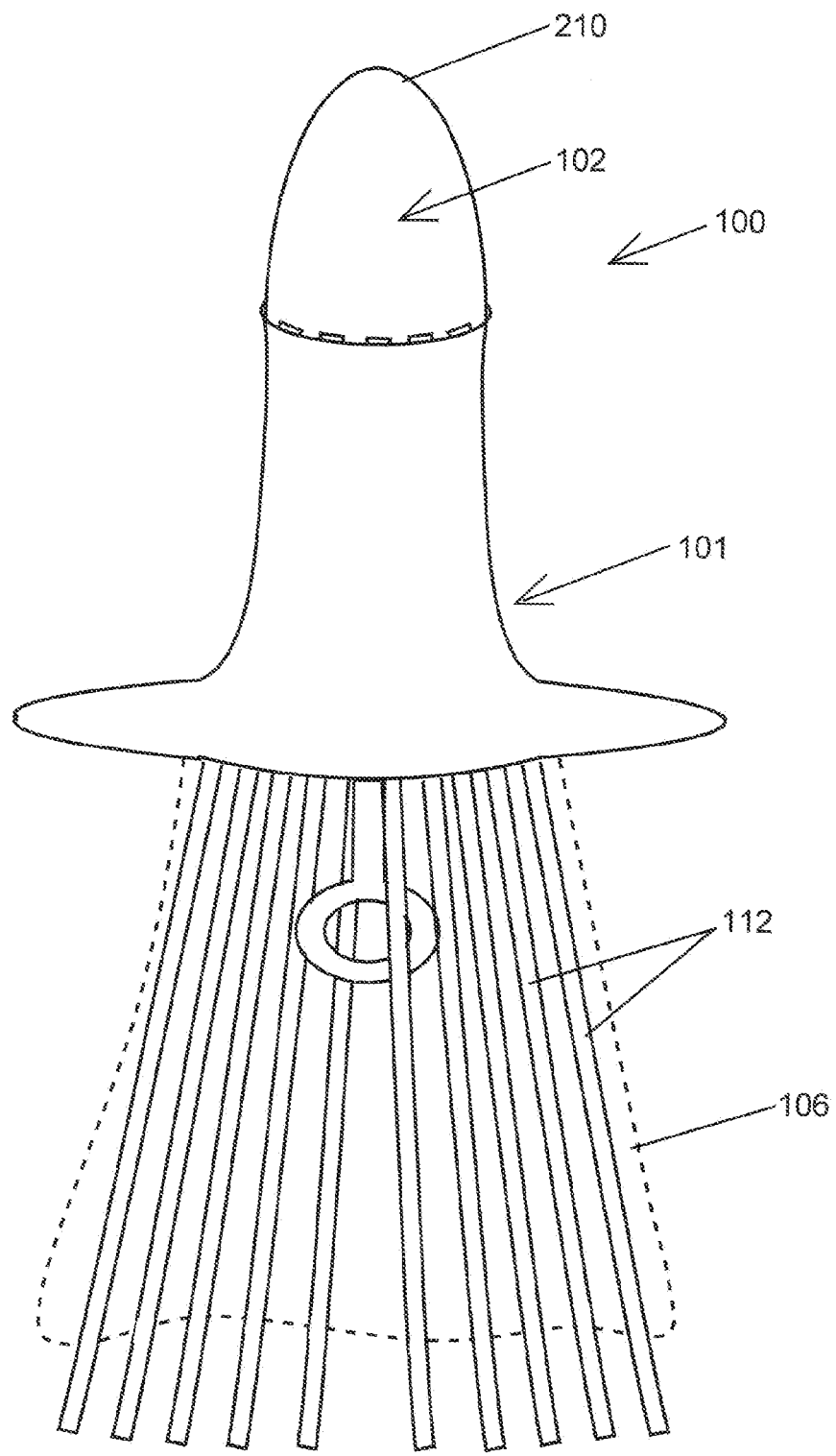
Figure 3B:
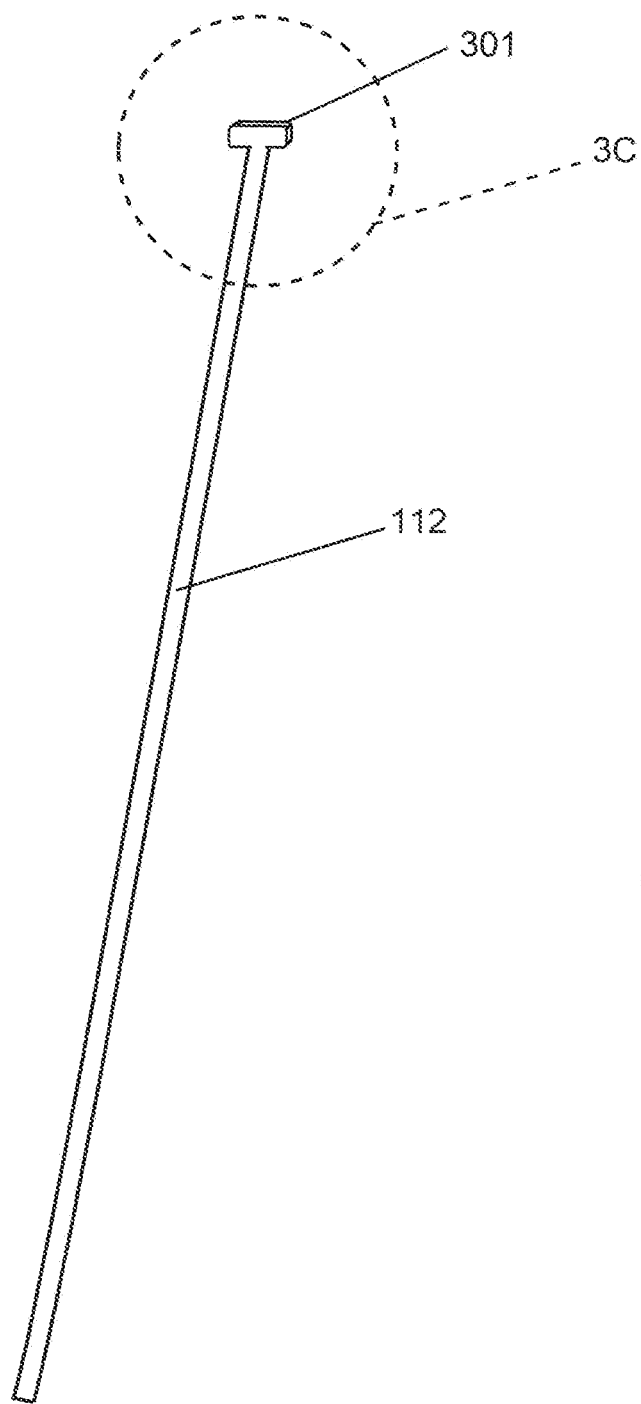
Figure 3C:
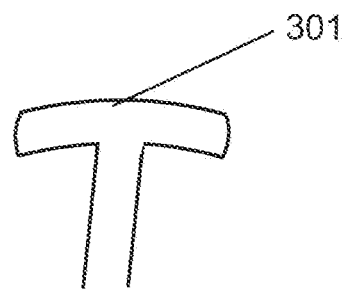

As shown in FIGS. 1-3, the base member 101 includes guideslots 110 separated by shelves 105 that can provide support for the tips 301 of the ribs 112. The base member 101 also includes peripheral flanges 204 at its bottom end to restrict the extent of its passage into a patient's anus. The base member 101 is formed of relatively hard plastic and its upper leading portion 206, which is inserted into a rectal cavity, has a diameter that is small enough to enable the base member 101 to be inserted through an anus and into a rectal cavity without damaging the anus or rectal cavity, yet large enough to accommodate a sigmoidoscope through it if necessary to ensure safety if direct viewing of the procedure is required.

Figure 4:
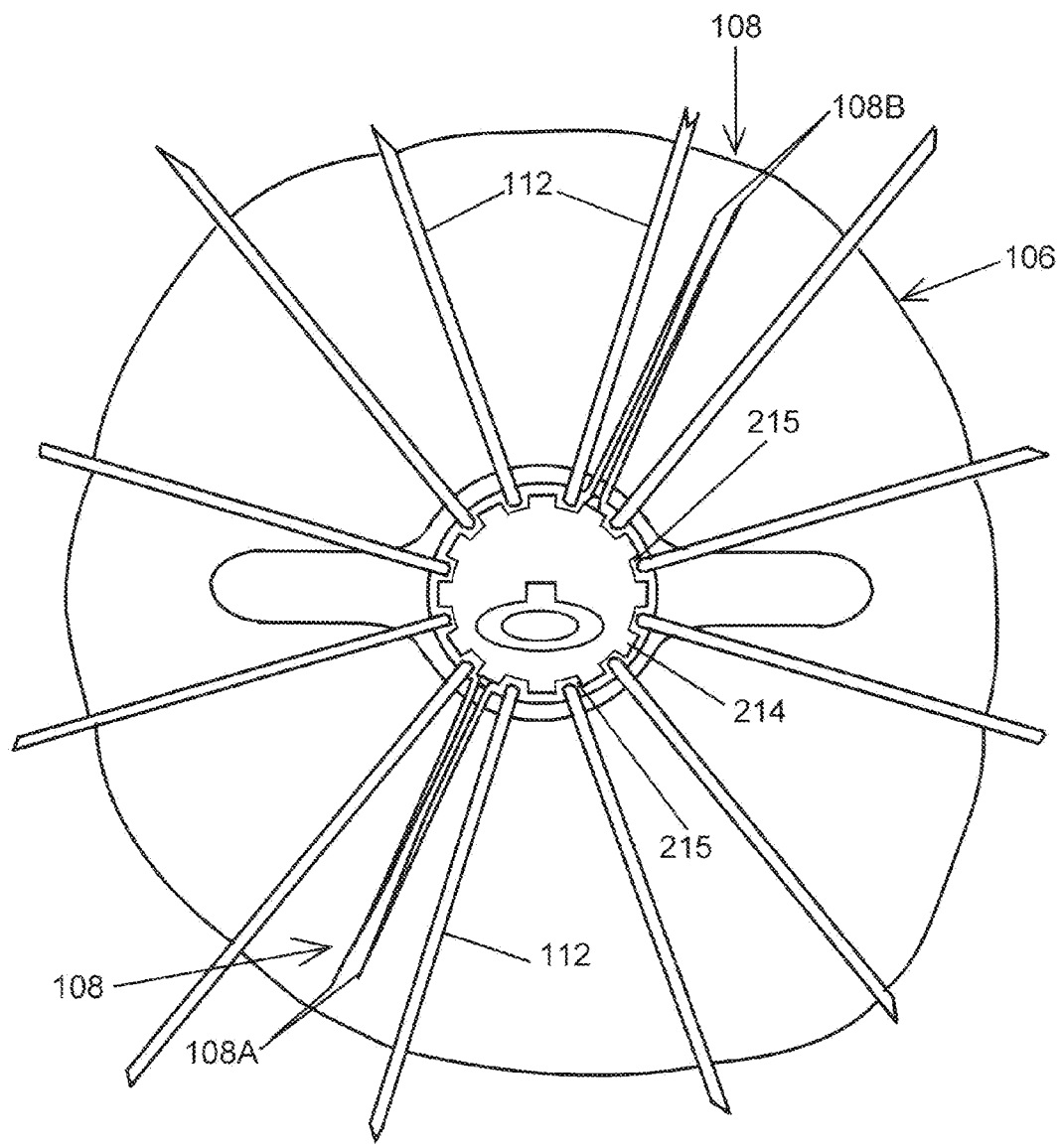
FIG. 4 schematically illustrates a view of additional parts of an apparatus for removing a foreign object from a rectal cavity, according to the invention.

The anoscope base includes an introducer 102 that has a rounded leading end 210 that extends out of and forward of the base member 101. The introducer has a shaft 212, a skirt 214 and a handle 216 that are connected with each other. The handle 216 extends out of the base member and would be located outside the patient's anus, so that the anoscope base can be manipulated (i.e. inserted and withdrawn from a patient's anus) from outside the patient's anus. The skirt 214 includes an array of guide slots 215, to help guide the flexible ribs 112 as those ribs are being manipulated by an operator to extend and expand the flexible sheath 106 about a foreign object in the rectal cavity. The introducer 102 is formed of the same hard plastic as the base member 101, and is connected with the base member such that the introducer effectively forms a part of the anoscope base. In this application, reference to parts such as the base member and introducer (or the introducer shaft, skirt and handle) being "connected with" each other encompasses the parts being separately formed and joined together by a cohesive pressure sizing so that they move as a unit, but are easily disattached for their intended use, and are parts formed in individual pieces (e.g. by injection molding) and assembled as a unit prior to use The flexible ribs 112 extend into the base member 101 and inside the closed inside border of the flexible sheath 106, so that the flexible ribs 112 and sheath are carried by the anoscope base as the anoscope base is inserted into a rectal cavity. In addition, the flexible noose 108 (i.e. noose strands 108A, 108B) is carried by the looped portion 300 of the flexible sheath as it is expanded by the flexible ribs, and once the flexible sheath has been expanded to extend about a foreign object in a rectal cavity, the portions of the noose that extend out of the looped portion of the sheath at the diametrically opposed locations can be manipulated to draw the flexible sheath closed above the foreign object (see e.g. FIGS. 5g, 5h). The noose 108 can then be manipulated to close the flexible sheath proximal to and about the foreign object within the rectal cavity, allowing the sheath to then form an enclosure within which the foreign object may be safely retracted distally and removed from the rectal cavity FIG. 4 schematically illustrates the operation of the flexible ribs 112 and noose 108 after the anoscope base has been inserted into a rectal cavity. The flexible ribs 112, flexible sheath 106 and noose 108 would be assembled with the anoscope base outside a rectal cavity, with the flexible ribs 112 located inside the closed border of the sheath and the noose 108 is carried by the looped portion of the flexible sheath as it is expanded by the flexible ribs. The flexible ribs 112 and the noose would be guided by the guide slots 215 in the skirt 214, and between the guideslots 110, with the tips 301 of the flexible ribs (that are inside the closed border of the sheath) located and supported on the shelves 105 of the base member 101. The ribs have a bias and a curvature such that when clear of the base member they separate in a manner that expands the flexible sheath 106. Once the anoscope has been assembled with the flexible ribs 112, flexible sheath 106 and flexible noose 108, and the anoscope inserted into a patient's rectal cavity, the introducer portion 102 can be removed and the flexible ribs, the flexible sheath 106 and the flexible noose strands 108A, 108B can be manipulated by an operator from outside the patient's rectal cavity, to extend beyond the guideposts and further into a rectal cavity, where they can expand and expand the flexible sheath about a foreign object in the rectal cavity. As the sheath is manipulated and expanded and advanced about the foreign object, it carries with it the flexible noose 108 that is connected with the sheath. The process may be preferably viewed by a fluoroscope, and once the radiopaque noose is seen by fluoroscopy to be proximal to the foreign body with traction on the flexible noose, it (actually the noose portions 108A, 108B) that extend out of the diametrically opposed locations of the looped portion 300) is (are) manipulated with tension to separate the leading closed portion of the sheath from the tips of the flexible ribs and tighten the flexible sheath into a tense knot. The anoscope base (by means of the flanges 204) and flexible ribs are then removed from the patient, and the flexible noose 108 is then manipulatable from outside the patient's rectal cavity to tighten and stricture the flexible sheath 106 above the foreign object and capture the foreign object within the flexible sheath, so that the foreign object can be manipulated by the noose and the flexible sheath tracted distally to remove the foreign object from the rectal cavity through the anus.

As shown in the schematics of FIG. 5 (*a-h*), the flexible sheath 106 is doubled over the noose 108 and sealed to form the closed loop 300 that carries the noose strands 108A, 108B, so that the noose is carried by the flexible sheath and as the noose is manipulated, effectively pulled slightly toward the exit of the rectal cavity, the noose frees the sheath from the tips of the flexible ribs, and further traction tightens and strictures the flexible sheath 106 above the foreign object and captures the foreign object within the flexible sheath, so that the foreign object can be manipulated by the noose and the flexible sheath to remove the foreign object from the rectal cavity.

FIG. 6 schematically shows the method of the invention for removing a foreign object from a rectal cavity.
 a. the anoscope base (that includes the base member 101 and introducer 102) is lubricated and then inserted into a rectal cavity, and carries the flexible members 112, noose 108 and the flexible sheath 106 that are configured to extend from the anoscope base further into a rectal cavity and to expand about a foreign object in the rectal cavity;
 b. the anoscope base carries the noose 108 that is manipulated from outside the rectal cavity to draw the noose and close the flexible sheath 106 above the foreign object and capture the foreign object within the flexible sheath, which are then manipulated in a manner that manipulates the foreign object distally to remove the foreign object from the rectal cavity once the anoscope base and flexible ribs are removed.

In the preferred way of practicing the method of the present invention, Once the loop 108 is tightened, the anoscope base, base member and flexible members are withdrawn from the rectal cavity before the noose and flexible sheath are manipulated to manipulate the foreign object distally and deliver it from the rectal cavity.

In addition, with the applicants device and method, if the foreign body to be removed is in any way dangerous or challenging, the configuration of the anoscope is made of such internal diameter that it will allow local observation of the entire procedure with a sigmoidoscope inserted through the verge of the anoscope 206 into the rectal space during performance of the method.

Thus, the foregoing detailed description provides an apparatus and method designed to remove a foreign object from a rectal cavity. With the foregoing disclosure in mind, the manner in which an apparatus can be designed, and a method practiced, to remove various types of foreign objects from a rectal cavity will be apparent to those in the art.

The invention claimed is:

1. A method for removing a foreign object from a rectal cavity, comprising
 a. providing an anoscope comprised of a base and an introducer portion that can be together inserted through the anus into a rectal cavity; where the introducer portion can be withdraw through the anus; the base of the anoscope carrying flexible members and a flexible sheath that are manipulated from outside the rectal cavity to extend the sheath from the base member and further into a rectal cavity and the flexible members and the flexible sheath configured to expand the sheath as it is being advanced further within the rectal cavity to extend about the foreign object in the rectal cavity; the flexible members carrying a noose that is manipulatable from outside the rectal cavity to draw the sheath closed above and about the foreign object;
 b. inserting the anoscope through an anus and into a rectal cavity, withdrawing the introducer portion and manipulating the flexible members and flexible sheath from outside the rectal cavity to extend the sheath through the base member and further into a rectal cavity expanding the sheath as it is being advanced further within the rectal cavity to extend above and about the foreign object in the rectal cavity; and
 c. manipulating the noose from outside the rectal cavity to draw the sheath closed above and proximal to the foreign object, and manipulating the noose and sheath together in such a manner that manipulates the foreign object that is within the flexible sheath to remove the foreign object from the rectal cavity through the anus.

2. The method of claim 1, wherein the anoscope base and flexible members can be withdrawn from the rectal cavity, and wherein the anoscope base and flexible members are removed from the rectal cavity once the noose is drawn closed above and about the foreign object and before the noose and sheath are then manipulated to capture the foreign object and remove it from the rectal cavity.

3. The method of claim 1, wherein the flexible sheath comprises a doubled-over sheath member that is sealed on itself at its leading edge to create a looped portion for the flexible noose, and the flexible members comprise flexible ribs that are disposed inside the doubled over sheath member, and the flexible ribs have tips located against the looped portion such that, once the introducer is removed from the anoscope base, the flexible ribs can be extended from the anoscope base further into a rectal cavity, and as they extend beyond the anoscope base and further into a rectal cavity they will expand the flexible sheath including the looped portion about a foreign object in the rectal cavity.

\* \* \* \* \*